US006602824B1

(12) United States Patent
Miles et al.

(10) Patent No.: US 6,602,824 B1
(45) Date of Patent: Aug. 5, 2003

(54) HERBICIDAL COMPOSITION AND A METHOD OF USING A NATURALLY-OCCURRING ORGANIC COMPOUND AS A HERBICIDE

(75) Inventors: Mark Miles, Woodbury, MN (US); James H. Powers, St. Paul, MN (US)

(73) Assignee: Greener Pastures Development Corp., St. Paul, MN (US)

( * ) Notice: Subject to any disclaimer, the term of this patent is extended or adjusted under 35 U.S.C. 154(b) by 0 days.

(21) Appl. No.: 09/425,105

(22) Filed: Oct. 12, 1999

Related U.S. Application Data

(60) Provisional application No. 60/120,432, filed on Feb. 16, 1999.

(51) Int. Cl.$^7$ .......................... A01N 33/12; A01N 65/00
(52) U.S. Cl. ....................... 504/150; 504/189; 504/345; 504/158
(58) Field of Search ............................... 504/158, 345, 504/150, 189

(56) References Cited

U.S. PATENT DOCUMENTS

| | | | | |
|---|---|---|---|---|
| 5,922,649 A | * | 7/1999 | Pehu et al. ................. | 504/320 |
| 5,952,267 A | * | 9/1999 | Mottram ..................... | 504/320 |
| 6,083,876 A | | 7/2000 | Jokinen et al. ............. | 504/147 |
| 6,281,411 B1 | | 8/2001 | Adams et al. .............. | 800/288 |
| 6,453,610 B2 | * | 9/2002 | Tonkin et al. ............... | 47/66.7 |

FOREIGN PATENT DOCUMENTS

| | | | |
|---|---|---|---|
| JP | 53-20422 | * | 2/1978 |
| JP | 58-116475 | * | 7/1983 |
| JP | 62-135489 | * | 6/1987 |

OTHER PUBLICATIONS

Derwent Abstract 1997–191106 of Lazarenkov, RU 2065678, Aug. 1996.*
Kirk–Othmer. Encyclopedia of Chemical Technology, 4th ed. John Wiley & Sons. vol. 23, p. 44–63 ("Beet Sugar") and 602–604 ("Syrups: Molasses"). 1997.*
Mauseth, James D. Botany: An Introduction to Plant Biology. Saunders College Pub. p. 186. 1995.*
Anderson, W. P. Weed Science. 3rd ed. West Pub. Co. Minneapolis/St. Paul. p. 18–20, 1996.*
Role of Quarternary Ammonium and Tertiary Sulfonium Compounds, Pathway(s) of Choline Synthesis, 2 pages, obtained from the Internet at address www.hort.purdue.ede/rhodcv/hort/640c/onium/on00002.htm, updated May 18, 1998 and obtained on Jul. 4, 1998.
Stress Responses in Microorganisms, Structure/function relationships of membrane proteins, DNA binding proteins and gene regulations, 5 pages, obtained from the Internet at address www.uni–marburg.de/microbiology/bremer/bremer.html, on Jul. 2, 1998.
Product Monograph CYSTADANE™ (betaine anhydrous powder for oral solution) Anti–Homocysteine Agent, 8 pages, obtained from the Internet at address www.mdmultimedia.com/html/CYSTADAN.htm, dated Jul. 12, 1998 and obtained from the Internet on Jun. 9, 1999.
What is Salt?, 4 pages, obtained from the Internet at address aacnt12.aac.com/salt–docs/15.html, on Jun. 4, 1999.
Compound betaine aldehyde, 5 pages, obtained from the Internet at address www–c.mcs.an1.gov/home/compbio/pum...ion/compoundobjects/betaine aldehyde.html, on Jul. 2, 1998.
Material Safety Data Sheet for sodium chloride supplied by Fisher Scientific Corporation, 5 pages, obtained from the Internet at address mc2.cchem.berkeley.edu/chem10/schloride.html, on Jun. 9, 1999.
Gorham, John, "Glycinebetaine is a Major Nitrogen–Containing Solute in the Malvaceae", *Phytochemistry,* vol. 43, No. 2, pp. 367–369 (1996).
Researchers Find Gene that Protects Plants Against Drought, Discovery Could Also Mean 'Sweeter' Harvests for Farmers, 3 pages, obtained from the Internet at address www.a-grialt.com/marapr96/gene.html, on Jul. 2, 1998.
Stumpf, David K., and James W. O'Leary, "The Distribution of Na+, K+ and Glycinebetaine in *Salicornia Bigelovii*", *Journal of Experimental Botany,* vol. 36, No. 165, pp. 550–555, Apr. 1985.
Greener Pastures Product Brochure entitled Clarify Natural Algae Control, Aug. 1998, 2 pages.
Greener Pastures Product Brochure entitled Introducing NWC (Nature's Weed Control): Natural Based Post Emergent Broadleaf Control, Aug. 1998, 4 pages.
Greener Pastures Product Brochure entitled Greener Pastures Lake and Pond Products, Aug. 1998, 22 pages.
Greener Pastures Product Brochure entitled 1999 Product Catalog, Dec. 1998, 22 pages.
Acros Organics Specification Sheet for: Betaine, anhydrous, 98%, 1 page, obtained from the Internet at address www.fisher1.com, on Dec. 29, 1998.
Abstract of Osmotic Control of Glycine Betaine Biosynthesis and Degradation in *Rhizobium Meliloti,* 1 page, obtained from the Internet at address www.ncbi.nm.nih.gov/htbin–post/Entrez/query?uid=3290197&form=6&db=m&Dopt=b, on Jul. 4, 1998; abstract of *J. Bacteriol.* 170(7):3142–3149. Jul., 1988.

(List continued on next page.)

Primary Examiner—S. Mark Clardy
(74) *Attorney, Agent, or Firm*—Kinney & Lange, P.A.

(57) ABSTRACT

A method of controlling unwanted plants, the method including providing an herbicidal composition, the herbicidal composition containing at least a naturally-occurring, plant-derived organic compound, and applying the herbicidal composition to the unwanted plants.

45 Claims, 3 Drawing Sheets

(3 of 3 Drawing Sheet(s) Filed in Color)

OTHER PUBLICATIONS

Abstract of Transformation of *Arabidopsis Thaliana* with the CodA Gene for Choline Oxidase; Accumulation of Glycinebetaine and Enhanced Tolerance to Salt and Cold Stress, 1 page, obtained from the Internet at address www.ncbi.nlm.nih.gov/htbin–post/Entrez/query?uid=9263456&form=6&db=m&Dopt=b, on Jul. 4, 1998, From *Plant. J.* 12(1):133–142 Jul. 1997.

Abstract of Glycinebetaine Enhances and Stabilizes the Evolution of Oxygen and the Synthesis of ATP by Cyanobacterial Thylakoid Membranes, 1 page, obtained from the Internet at address www.ncbi.nlm.nih.gov/htbin–post/Entrez/query?uid=1756870form=6&db=m&Dopt=b, on Jul. 4, 1998, from *FEBS Lett.* 294(3):271–274, 12/91.

Chin Bum Lee, Hidenori Hayashi and Byoung Yong Moon, "Stabilization of Glycinebetaine of Photosynthetic Oxygen Evolution by Thylakoid Membranes from Synechococcus PCC7002", *Mol. Cells,* vol. 7, No. 2, pp. 296–299 (1997).

*Beta Vulgaris,* 3 pages, obtained from the Internet at address http://ifs.plants.ox.ac.uk/fao/tropfeed/data/r524.htm, on Jun. 26, 1998.

Abstract of Near–isogenic Lines of Maize Differing for Glycinebetaine, 1 page, obtained from the Internet at address www.ncbi.nlm.nih.gov/htbin–post/Entrez/query?uid=7724675&form=6&db=m&Dopt=b, on Jul. 4, 1998; from *Plant Physiol.* 107:621–630. 1975.

Douglas M. Webel, Effect of Betaine in Finishing Pigs, 1 page, obtained from the Internet at address www.aces.uiuc.edu/~pork/research/betaine.html, on Jul. 2, 1998; from 1995 Swine Research Report.

Abstract of Crop Production Under Stress Conditions, 1 page, obtained from the Internet at address honeybee.helsinki.fi/mmkat/kvil/projects/pmregula.htm, on Jul. 4, 1998; Project finished Dec. 1996.

Abstract of Osmotic Stress Induces Expression of Choline Monoxygenase in Sugar Beet, 2 pages, obtained from the Internet at address www.sheridan.com/aspp/abs/45/0195.html, on Jul. 4, 1998.

Abstract of Quantitative Role of Glycine Betaine and DMSP in Cellular Nitrogen and Sulfur Budgets of Marine Phytoplankton, 1 page, obtained from the Internet at address www.best.com/~workline/c/12/185c.htm, on Jul. 4, 1998.

Abstract of Csonka, L.N., Physiological and Genetic Responses of Bacteria to Osmotic Stress, 1 page, obtained from the Internet at address www.ncbi.nlm.nih.gov/htbin–post/Entrez/query?uid=2651863&form=6&db=m&Dopt=b, on Jul. 4, 1998; from *Microbiol. Rev.* 53(1):121–147, Mar. 1989.

Fertilizer Fundamentals, 6 pages, obtained from the Internet at address www.espoma.com/pages/fertilizer_fundamentals.html, on Apr. 19, 1999.

Enzymes and Genes of Glycinebetaine Synthesis, 1 page (pp. 2 & 3 missing), obtained from the Internet at address www.hort.purdue.edu/rhodcv/hort640c/onium/on00004.htm, on Jul. 4, 1998.

Structures of Intermediates Involved in Glycinebetaine Synthesis, 1 page, obtained from the Internet on Jul. 4, 1998 at address www.hort.purdue.edu/rhodcv/hort640c/onium/on00003.htm, last updated on May 18, 1998.

Pathway(s) of Choline Synthesis, 2 pages, obtained from the Internet on Jul. 4, 1998 at address www.hort.purdue.edu/rhodcv/hort640c/onium/on00002.htm, last updated on May 18, 1998.

Role of Quarternary Ammonium and Tertiary Sulfonium Compounds as Compatible Solutes, 2 pages, obtained from the Internet on Jul. 4, 1998 at address www.hort.purdue.edu/rhodcv/hort640c/onium/on00001.htm, last updated 18, 1998.

Glycinebetaine: A Solution for Cotton Production in Drought Prone Areas?—What Is Glycinebetaine (GB or GlyBet)?, 3 pages, obtained from the Internet at address http://achilleus.tamu.edu/personal/Philip/PhilWebWhat_is1.htm on Jul. 4, 1998.

Glycinebetaine: A Solution for Cotton Production in Drought Prone Areas?—Drought tolerance, 2 pages, obtained from the Internet at address http://achilleus.tamu.edu/personal/Philip/PhilWeb/Drought.htm on Jul. 4, 1998.

Glycinebetaine from Sugar Beet Enhances the Yield of Field–Grown Tomatoes, 6 pages, obtained from the Internet at address achilleus.tamu.edu/personal/philip/philweb/jokinen.htm, on Jul. 4, 1998.

Metabolic Engineering of Crops for Drought and Salt Tolerance, 2 pages, dated Jun., 1998, obtained from the Internet at address www.reeusda.gov/nri/pubs/highlights/jun98/jun98.htm, on May 6, 1999.

Lorenzi, Harry J., and Larry S. Jeffrey. *Weeds of the United States and Their Control,* pp. 1–23, Van Nostrand Reinhold Company, NY, 1987.

Bradow, Judith M., Christopher P. Dionigi, Richard M. Johnson and Suhad Wojkowski. "Herbicides" in *Kirk–Othmer Encyclopedia of Chemical Technology,* vol. 13, $4^{th}$ Edition, pp. 73–123, John Wiley & Sons, NY, 1985.

Frankel, Paul, and Terri Mitchell, *Personal Reports and Long–Term Use,* Dated Jul. 1997, 2 pages.

Frankel, Paul, and Terri Mitchell, *Vitamin $B_6$ and Homocysteine,* Dated Jul. 1997, 3 pages.

Search Report, American Chemical Society, Chemical Abstracts, conducted on Jan. 4, 1999, 40 pages (missing p. 19 of 40).

Search Report from DIALOG® database, conducted on Feb. 24, 1999, 7 pages.

Search Report from DIALOG® database, conducted on Feb. 24, 1999, 13 pages.

Search Report, database unknown, conducted on Jan. 4, 1999, 27 pages (missing pp. 2 of 27, 8 of 27, and 9 of 27).

Zamarreño, A., R. G. Cantera and J. M. Garcia–Mina. Extraction and Determination of Glycinebetaine in Liquid Fertilizer. 1997. *Journal of Agric. Food Chem.,* 45, pp. 774–776.

Abstract of Exogenously applied glycinebetaine affects photosynthetic processes of turnip rape plants (*Brassica rapa* ssp. *oleifera*) grown under water deficiency, Phytochemical Society of Europe, International Symposium on Regulation of Primary Metabolic Pathways in Plants, St. Hugh's College, Oxford, United Kingdom, Jan. 9–11, 1997.

Christians, Nick. A Natural Product for the Control of Annual Weeds, Gold Course Management, Oct. 1993 (3 pages).

Christians, N. E., The Use of Corn Gluten Meal as a Natural Preemergence Weed Control In Turf, International Turfgrass Society Research Journal, 1993, pp. 284–290.

Liu, Dianna Lan–Ying, Nick E. Christians, John T. Garbutt, Herbicidal Activity of Hydrolyzed Corn Gluten Meal on Three Grass Species under Control Environments, Journal of Plant Growth Regulation, 1994, pp. 221–226.

Liu, D. L. and N. E. Christians, *Biochemistry of a Pentapeptide Isolated from Corn Gluten Hydrolysate on Lolium perenne* L., Journal of Plant Growth Regulation (1996) 15: 13–17.

Liu,, Dianna Lan–Ying and Nick E. Christians, Isolation and Identification of Root–Inhibiting Compounds from Corn Gluten Hydrolysate, Journal of Plant Growth Regulation (1994) 13: 227–230.

Bingaman, Barbara R. and Nick E. Christians. Greenhouse Screening of Corn Gluten Meal as a Natural Control Product for Broadleaf and Grass Weeds. 1995. Hortscience 30(6): 1256–1259.

* cited by examiner

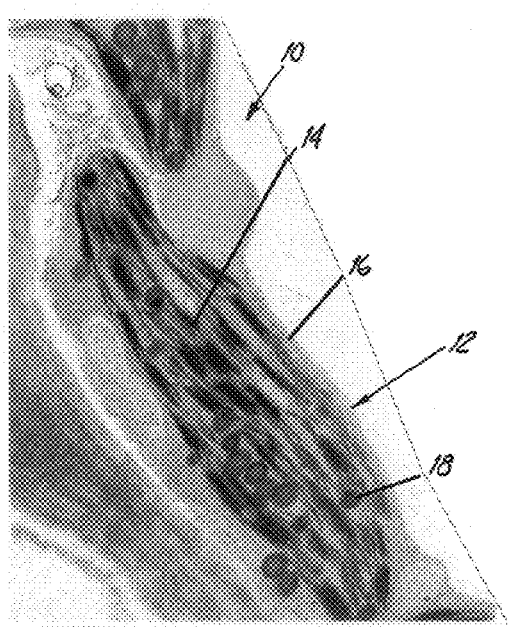
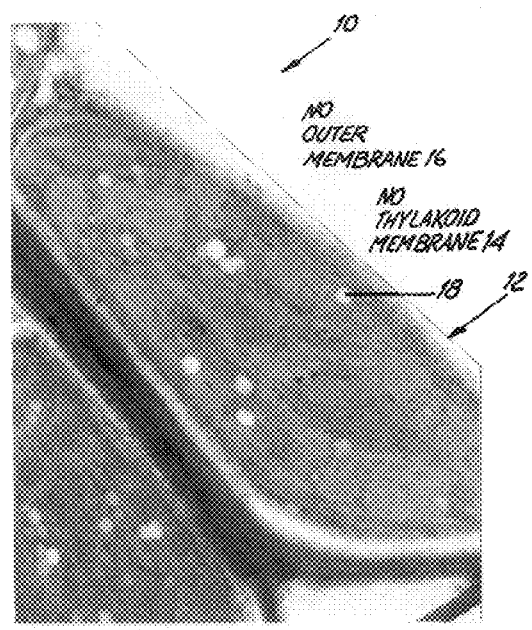
Fig. 1
Fig. 2

HERBICIDAL COMPOSITION AND A METHOD OF USING A NATURALLY-OCCURRING ORGANIC COMPOUND AS A HERBICIDE

CROSS-REFERENCE TO RELATED APPLICATION(S)

Application Ser. No. 60/120,432 filed on Feb. 16, 1999.

BACKGROUND OF THE INVENTION

The present invention generally relates to an herbicidal composition and to a method of using a naturally-occurring, plant-derived organic compound as a herbicide. More particularly, the present invention relates to an herbicidal composition that includes the naturally-occurring, plant-derived, organic compound and to a method of using the naturally-occurring, plant-derived, organic compound to control aquatic and terrestrial weeds.

A weed may be generally defined as an unwanted terrestrial or aquatic plant. Conversely, a terrestrial or aquatic plant that is desired is not a weed, but is instead a desirable plant. Weeds often interfere with efficient utilization of land and water resources and typically compete with desired plants for water, nutrients, light, carbon dioxide, and space. Many weeds are also aesthetically displeasing, especially when the weeds appear within a stand of a desired plant, such as St. Augustine grass or Kentucky bluegrass in a homeowner's lawn. Weeds may also obstruct visibility, become fire hazards around buildings, and reduce the efficiency of irrigation systems. When weeds appear in watercourses, such as rivers and lakes, the weeds may contribute to poor water quality, making the water unsuitable for culinary and industrial uses. Furthermore, some weeds act in a poisonous fashion against other plants, animals, and humans by secreting toxic substances known as alleopathic compounds or by spreading agents that may cause allergies and/or disease. Finally, weeds provide shelter for insects and rodents that spread disease or are otherwise harmful to desired plants, animals, or humans.

Weeds cause agricultural losses to crops that consistently exceed losses caused by other classes of agricultural pests, year after year. Besides reducing the quality of the crop, weed infestation may reduce achievable crop yield by up to 100% of the theoretically achievable yield. A number of approaches, including mechanical, agricultural, biological, and chemical techniques, have evolved in an attempt to control weed infestation.

Mechanical means, such as hand pulling, hoeing or cultivation, deep plowing, clipping, mowing, burning and/or mulching, may be employed in an attempt to eradicate or control weeds. Also, cover crops may be planted to keep the ground covered when not growing more valuable crops and thus weed infestation that would ordinarily be expected to occur in bare ground areas is typically minimized. Crop rotation and planting of "smother" crops that are adapted to grow more vigorously than weeds have also been attempted as means of controlling weed infestations. Besides these mechanical and agricultural techniques, biological methods of weed control, such as introduction of predator populations that feed on the weeds and thereby reduce weed population, have also been attempted.

Mechanical, agricultural, and biological methods of weed control, while sometimes helping to reduce the extent of weed infestations, are not fully satisfactory. First, mechanical and agricultural techniques are quite labor intensive and require use of limited physical and capital resources. Furthermore, environmental factors beyond the control of the farmer or homeowner, such as excessive rainfall, may diminish the effectiveness of these mechanical and agricultural techniques. Likewise, biological techniques, such as introduction of predator populations, are not entirely satisfactory, since the predators may not be selective for only the weed population.

Chemically active herbicides represent another potential weed control technique. These chemical herbicides may be broken down into pre-emergent herbicides and post-emergent herbicides. Pre-emergent herbicides typically interfere with germination of weed seeds, whereas post-emergent herbicides kill the weeds after the weed seeds have germinated and weed growth has begun.

Pre-emergent herbicides may be effective when present at the required dosage at the time weed seed germination is ready to occur. However, this timing issue points out a major problem with respect to pre-emergent herbicides. Specifically, if the pre-emergent herbicide is not applied, or degrades, prior to weed seed germination, the weed seeds are free to germinate and begin growing into mature weeds. Additionally, pre-emergent herbicides are typically weed specific and are not equally effective against all types of weeds. The timing problem present with pre-emergent herbicides may be avoided by employing post-emergent herbicides and by applying the post-emergent herbicide only after the weed seeds have germinated and the weeds are actively growing. However, many presently available post-emergent herbicides are non-selective herbicides and therefore will kill desirable plants in addition to weeds.

Many pre- and post-emergent herbicides also suffer from another problem. Specifically, many pre-emergent herbicides and post-emergent herbicides are either moderately or highly toxic to humans and animals, and may thereby have damaging effects far beyond the intended weed control effect. Toxic herbicides may cause injury either immediately or over the long term to persons applying the herbicides and to persons present when the herbicides are applied. Also, residual concentrations of toxic herbicides that remain in the soil or water after application of the herbicide may pose a significant threat to human beings and to animals, including land-based animals and amphibians and fish, upon contact with the treated area or runoff from the treated area. Furthermore, public alarm about the use of toxic chemicals as herbicides and their potential widespread and long-term effects on environmental quality dictate against the continued use of these toxic herbicides.

There is a need for an herbicidal solution that avoids the critical timing issues of pre-emergent herbicide applications. Furthermore, there is a need for an herbicidal solution that avoids the toxic effects of presently available pre-emergent and post-emergent herbicides on human beings, animals and the environment generally. Furthermore, there is a need for an economically efficient post-emergent weed technique that selectively controls weeds without destroying or hindering the growth of desired plants.

BRIEF SUMMARY OF THE INVENTION

The present invention includes a method of controlling unwanted plants. The method includes providing an herbicidal composition that contains at least a naturally-occurring, plant-derived organic compound and applying the herbicidal composition to the unwanted plants. The present invention further includes an herbicidal composition and a method of increasing water clarity in a body of water.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a photomicrograph of chloroplasts of a healthy, actively growing weed prior to treatment of the weed with an aqueous herbicidal composition that contains glycine betaine.

FIG. 2 is a photomicrograph of the weed chloroplasts depicted in FIG. 1 after treatment of the weed in accordance with the present invention using the aqueous herbicidal composition that contains glycine betaine.

DETAILED DESCRIPTION

Figure 3:
FIG. 3 is a photograph of weeds present in a field before treatment with the aqueous herbicidal composition that contains glycine betaine.

The present invention generally relates to a method of using a naturally-occurring, plant-derived organic compound to control terrestrial and aquatic weeds. More specifically, the present invention relates to a method of using the naturally-occurring, plant-derived organic compound for both pre-emergent and post-emergent control of terrestrial and aquatic weeds.

The naturally-occurring, plant-derived organic compound, which is preferably glycine betaine, may be generally characterized as a quarternary ammonium salt, such as the quartenary ammonium salt depicted in graphic formula I below:

I where $R_1$, $R_2$, and $R_3$ may each be methyl groups and where $R_4$ may be a carboxylate ion group, such as the carboxylate ion group depicted in graphic formula II below:

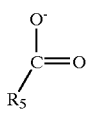

II where $R_5$ may be $CH_2$ when the group of formula II is substituted as $R_4$ in formula I. Thus, one particular form of the quarternary ammonium salt that may be used as the naturally-occurring, plant-derived organic compound in accordance with the present invention may be the compound that is graphically represented in formula III below:

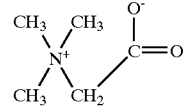

III

The compound depicted in graphic formula III is commonly referred to as glycine betaine, and is also known as 1-carboxy-N,N,N-trimethylmethanaminium inner salt. Glycine betaine may be derived from a number of different plant sources, such as from sugar beets.

As used herein, the term "naturally-occurring, plant-derived organic compound" means an organic compound that originated in a living organism of the plantae kingdom and that has not been altered molecularly from the molecular structure of the organic compound when present in the living organism. All references to "naturally-occurring, plant-derived organic compound" are also to be understood as encompassing any synthetically-produced identical copy of the organic compound that is identical in molecular structure to the organic compound that originated in a living organism of the plantae kingdom.

Besides glycine betaine, it is believed that other betaines, such as alanine-betaine, proline-betaine, histidine-betaine, tryptophan-betaine and pipecholate-betaine, provide herbicidal control activity and are consequently suitable additional non-exhaustive examples of the naturally-occurring, plant-derived organic compound that may be used to control terrestrial and aquatic weeds in accordance with the present invention. Like glycine betaine, the other betaines, such as alanine-betaine, proline-betaine, histidine-betaine, tryptophan-betaine and pipecholate-betaine, may be derived from a number of different plant sources. Though subsequent references to the naturally-occurring, plant-derived organic compound specifically address glycine betaine, it is believed that other betaines, such as alanine-betaine, proline-betaine, histidine-betaine, tryptophan-betaine, pipecholate-betaine, and any of these listed betaines in any combination may be substituted in place of, or used in any combination with, glycine betaine for control of terrestrial and aquatic weeds in accordance with the present invention.

Glycine betaine may be used to kill many types of terrestrial (growing in soil) and aquatic (growing in water) weeds in accordance with the present invention. As used herein, the term "weed" means an unwanted plant. Unwanted plants may be further classified as terrestrial weeds and aquatic weeds. Both pre-emergent and post-emergent control of terrestrial and aquatic weeds are typically obtained when glycine betaine is applied in accordance with the present invention.

As an example, glycine betaine, when applied in accordance with the present invention, is effective for pre-emergent control and post-emergent control of any dicotyledonous plants that are viewed as undesirable and, thus unwanted plants, or weeds. Some non-exhaustive examples of dicotyledonous plants that are typically terrestrial in nature and that may be selectively controlled by pre-emergent and post-emergent application of glycine betaine in accordance with the present invention include creeping Charlie (*Glechoma hederaceae*), black medic (*Medicago lupulina*), black nightshade (*Solanium nigrum*), buckhorn plantain (*Plantago lanceolata*), catchweed bedstraw (*Galium aparine*), common lambsquarters (*Chenopodium album*), curly dock (*Rumex crispus*), dandelion (*Taraxacum officinale*), purslane (*Portulaca oleracea*), redroot pigweed (*Amaranthus retroflexus*), and velvet leaf (*Abutilon theophrasti*).

Additionally, when applied in accordance with the present invention, glycine betaine is effective for pre-emergent control of any unwanted monocotyledonous plant and for post-emergent control of any unwanted monocotyledonous plant that has not reached the post-embryonic state. Some non-exhaustive examples of monocotyledonous plants that may be selectively controlled by pre-emergent application, as well as by post-emergent application if the monocotyledonous plant that has not reached the post-embryonic state, of glycine betaine in accordance with the present invention include crabgrass (*Digitaria sanguinalis*) and quackgrass (*Agropyron repens*). As used herein, a monocotyledonous plant that has not reached the post-embryonic state is defined as a monocotyledonous plant that has germinated and has not surpassed the three-leaf stage or, for monocotyledonous plants that do not develop more than three leaves, has not yet reached a height of about two inches above the growing medium (i.e.: is less than about two inches above the growing medium).

Some non-exhaustive examples of plants that are typically aquatic in nature and that may be selectively killed by pre-emergent and post-emergent application of glycine betaine in accordance with the present invention include Duckweed (Lemna spp.) and filamentous algae, such as Spirogyra, Chlamydomonas, *Eurasian milfoil* and Oedogonium. Furthermore, other algae, such as algae responsible for diminished water clarity in the aquatic environment, may also be controlled by application of glycine betaine. Some non-exhaustive examples of algae responsible for diminished water clarity in the aquatic environment that may be controlled with the application of glycine betaine in accordance with the present invention include planktonic algae, such as diatoms, dinoflagellates, and naked flagellates.

Surprisingly, even though terrestrial and aquatic dicotyledonous weeds are controlled via application of glycine betaine in accordance with the present invention, such application of glycine betaine does not harm aquatic, amphibious, or terrestrial animals. In fact, animals that are exposed to glycine betaine during application of glycine betaine in accordance with the present invention actually benefit from this exposure.

For example, when aquatic animals, such as salmon, are exposed to glycine betaine during or after application of glycine betaine to aquatic weeds or weed seeds in accordance with the present invention, enhanced osmotic regulatory properties, such as increased tolerance to fluctuating salt concentrations, are observed in the aquatic animals. Furthermore, the naturally-occurring, plant-derived organic compound, such as glycine betaine, has a very low degree of toxicity and therefore does not harm aquatic, amphibious, or terrestrial animals when applied to weeds in accordance with the present invention. The $LD_{50}$, short for "lethal dose 50", is a measure of the amount of a substance, administered in a single dose, that causes the death of 50% of an animal population from exposure to the substance by any route other than inhalation. $LD_{50}$ is usually expressed as milligrams or grams of material per kilogram of animal weight (mg/kg or g/kg). The naturally-occurring, plant-derived organic compound preferably has an $LD_{50}$ that is greater than about 11,000 mg of the naturally-occurring, plant-derived organic compound per kilogram of rat body weight when the naturally-occurring, plant-derived organic compound is orally administered to rats.

Glycine betaine meets this criteria, since the $LD_{50}$ of glycine betaine is about 11,204 mg of glycine betaine per kilogram of rat body weight when the glycine betaine is orally administered to the rats. On the other hand, the $LD_{50}$ of sodium chloride, ordinary table salt, is about 3,000 mg of sodium chloride per kilogram of rat body weight when the sodium chloride is orally administered to the rats. Thus, the toxicity of glycine betaine, as reflected by the $LD_{50}$ for a dose that is orally administered to rats, is more than three times less toxic than ordinary table salt. Consequently, the naturally-occurring, plant-derived organic compound, such as glycine betaine, may be applied in accordance with the present invention to control weeds, such as dicotyledonous plants and immature monocotyledonous plants, while not harming aquatic, amphibious, or terrestrial animals.

Likewise, even though terrestrial and aquatic dicotyledonous weeds are controlled via application of glycine betaine in accordance with the present invention, such application of glycine betaine does not harm post-embryonic monocotyledonous plants. As used herein, a "post-embryonic monocotyledonous plant" is defined as a monocotyledonous plant that has germinated and has surpassed the three-leaf stage or, for monocotyledonous plants that do not develop more than three leaves, has reached a height of about two inches, or more, above the growing medium.

Surprisingly, post-embryonic monocotyledonous plants that are exposed to glycine betaine during application of glycine betaine in accordance with the present invention actually benefit from this exposure. For example, post-embryonic monocotyledonous plants, when exposed to glycine betaine during application to weeds in accordance with the present invention, turn a rich green color and exhibit increased plant density, resistance to extreme temperature differences, frost resistance down to temperatures of about 14° F., salt-resistance, and drought-resistance. Many examples of monocotyledonous plants, such as annual bluegrass (*Poa annua*), St. Augustine's Grass (*Stenotaphrum secundatum*), Fescue (Festuca spp.), and Kentucky bluegrass (*Poa prathensis*), are perceived as desirable lawn grasses that may thus be benefitted when applying glycine betaine to control weeds in accordance with the present invention.

One dicotyledonous weed that is generally depicted at 10 in FIG. 1 and that may be controlled in accordance with the present invention is creeping Charlie (*Glechoma hederaceae*). The weed 10 is an actively growing weed that has not yet been treated with glycine betaine. When glycine betaine is applied to the weed 10 in accordance with the present invention, the glycine betaine increases the metabolic rate of photosynthesis in chloroplasts 12 of the weed 10. The chloroplasts 12 include both thylakoid membranes 14 and outer membranes 16.

Increasing the metabolic rate of photosynthesis in the chloroplasts 12 using glycine betaine in accordance with the present invention ruptures and destroys the thylakoid membranes 14 and outer membranes 16 of the chloroplasts 12. Thus, as best depicted in FIG. 2, the thylakoid membranes 14 (not visible in FIG. 2) and the outer membranes 16 (not visible in FIG. 2) of the weed 10 are indiscernible and unidentifiable after treatment of the weed 10 with glycine betaine in accordance with the present invention. The destruction of the thylakoid membranes 14 and outer membranes 16 of the chloroplasts 12 destroys the ability of the weed 10 to generate energy for metabolic processes, and the weed 10 is consequently killed. Bubbles 18 of oxygen are trapped in the chloroplasts 12 of the weed 10 being treated with glycine betaine. The presence of the bubbles 18 of oxygen that are trapped in the chloroplasts 12 are indicative of the increased rate of photosynthesis in the chloroplasts 12 that enhances the herbicidal activity of the glycine betaine in the weed 10.

When used for pre-emergent and/or post-emergent control of terrestrial weeds, glycine betaine may generally be applied in any form, such as in vapor or granular form, or as part of an aqueous herbicidal composition. The application form that is selected preferably permits the glycine betaine (1) to contact the terrestrial weeds and/or weed seeds being treated, (2) remain in contact with any growing terrestrial weeds being treated for at least several minutes, such as about 5 minutes, and (3) remain in contact with any terrestrial weed seeds being treated through the germination period.

The aqueous herbicidal composition may be based on an herbicidal concentrate. The herbicidal concentrate may include only glycine betaine and water or may optionally include additional components. The concentration of glycine betaine in the herbicidal concentrate may generally range from about 15 weight percent to about 47 weight percent, based on the total weight of the herbicidal concentrate. The herbicidal concentrate may optionally include additional components, such as sucrose, potassium, raffinose, sodium, fructose, calcium oxide, ash and any other components that are compatible with, and that do not interfere with, the herbicidal effect of glycine betaine.

A purified form of glycine betaine, such as Nutristim® purified glycine betaine, may be used to supply, or supplement, the glycine betaine content of the herbicidal concentrate. Nutristim® purified glycine betaine may be obtained from Finn Sugar Bio-Products of Helsinki, Finland and Schaumburg, Ill.

Alternatively, a glycine betaine-containing, plant-derived product, such as a molasses processing byproduct known as CONCENTRATED SEPARATED BY-PRODUCT (subsequently referred to as "CSB") that is available at the East Grand Forks, Minn. sugar beet processing plant of American Crystal Sugar Company may supply some, preferably most, and most preferably all, of the glycine betaine content of the herbicidal concentrate. CSB that is produced by American Crystal Sugar at the East Grand Forks, Minn. sugar beet processing plant may be obtained by contacting Midwest Agri-Commodities of Moorhead, Minn. Indeed, the plant-derived product, such as CSB, may be, and preferably is, the herbicidal concentrate. If the concentration of glycine betaine in the plant-derived product, such as CSB, is lower than about 15 weight percent to about 47 weight percent glycine betaine, based on the total weight of the plant-derived product, purified glycine betaine, such as that available from Finn Sugar Bio-Products, may be added to boost the glycine betaine concentration in the plant-derived product, such as CSB.

When CSB is used as the source of glycine betaine, the herbicidal concentrate may have the composition ranges for particular components that are specified in Table 1 below:

TABLE 1

| Component | Concentration (Weight Percent)* |
| --- | --- |
| Glycine betaine | about 15 to about 47 |
| Sucrose | about 60 to about 65 |
| Potassium | about 4 to about 5 |
| Raffinose | about 0.5 to about 1.5 |
| Sodium | about 0.5 to about 1.5 |
| Fructose | about 0 to about 1 |
| Calcium Oxide | about 0 to about 0.035 |
| Ash | about 9 to about 10 |

*based on the total weight of the herbicidal concentrate

One commercially available herbicidal concentrate that typically has the component concentration ranges specified in Table 1 may be obtained as NATURE'S WEED CONTROL™ herbicidal concentrate that is available from Greener Pastures Development Corporation of St. Paul, Minn. NATURE'S WEED CONTROL™ herbicidal concentrate is available either as a liquid or in granular form.

As mentioned earlier, glycine betaine may be included as part of the aqueous herbicidal composition for pre-emergent and/or post emergent control of terrestrial weeds. The aqueous herbicidal composition may contain only the herbicidal concentrate and water. However, the aqueous herbicidal composition may optionally include one or more sources of nitrogen in a form that is readily absorbed by growing terrestrial weeds. The optional source(s) of nitrogen, when used in combination with the aqueous herbicidal composition on terrestrial weeds, generally enhances the metabolic rate of weed growth. Increasing the weed growth rate enhances the uptake of glycine betaine by terrestrial weeds and thereby enhances the effectiveness of the aqueous herbicidal composition for post-emergent terrestrial weed control.

Alternatively, the optional source(s) of nitrogen may be applied separately from the aqueous herbicidal composition, either before, during, or after application of the aqueous herbicidal composition. Additionally, the source(s) of nitrogen may be applied in particulate form, as part of an aqueous solution, or in a vapor form, so long as the particular form selected results in nitrogen uptake by the terrestrial weed. One preferred source of nitrogen is LIQUID COMPOST™ 1-1-3 fertilizer, that may be obtained from Greener Pastures Development Corporation of St. Paul, Minn. Preferably, the glycine betaine, whether applied in granular or vapor form, or as part of the aqueous herbicidal composition, is applied in conjunction with the optional source of nitrogen to enhance the uptake of glycine betaine by the terrestrial weed.

The concentration of glycine betaine in the aqueous herbicidal composition may range from about 0.1 weight percent glycine betaine to about 20 weight percent glycine betaine based on the total weight of the aqueous herbicidal composition. The degree of weed control is maximized at the upper end of this range. Therefore, application at concentrations above the upper end of this range, while remaining effective for weed controls, would be wasteful and have little, if any, enhanced weed control effect.

As mentioned earlier, the optional nitrogen source(s) may be added to the aqueous herbicidal composition. In one preferred formulation, the aqueous herbicidal composition may contain about ½ cup of herbicidal concentrate, in the form of the liquid version of NATURE'S WEED CONTROL™ herbicidal concentrate; about 1 quart of LIQUID COMPOST™ 1-1-3 fertilizer; about 1 pound of urea, an optional source of nitrogen that may be obtained from Greener Pastures Development Corporation of St. Paul, Minn.; and about 0.7 to about 1.7 gallons, more preferably about 0.7 gallons, of tap water.

The aqueous herbicidal composition may be applied at any rate, expressed in gallons of aqueous herbicidal composition per thousand square feet, that is effective for some degree of pre-emergent and/or post-emergent control terrestrial weeds. Though even a low application rate on the order of about ¼ gallon per thousand square feet, or even lower, causes some degree of control of treated terrestrial weeds and/or weed seeds, higher application rates tend to increase the eradication effect of the aqueous herbicidal composition on terrestrial weeds, increase the suppression effect on weed seed germination and, consequently, cause better weed control.

Preferably, the aqueous herbicidal composition is applied to terrestrial weeds and/or weed seeds at a rate ranging from about ½ gallon per thousand square feet to about four gallons per thousand square feet, and is more preferably applied at a rate of about 1 gallon per thousand square feet. The application rate is based upon the square footage of the area to be treated, rather than upon the concentration of terrestrial weeds and/or weed seeds in the area to be treated. Any conventional lawn or agricultural spraying equipment may be used to apply the aqueous herbicidal composition to terrestrial weeds and/or weed seeds.

When used to control aquatic weeds and/or weed seeds, the glycine betaine may generally be applied in any form, such as in vapor or granular form, or as part of the aqueous herbicidal composition. The application form that is selected should permit the glycine betaine to (1) contact the aquatic weeds and/or weeds seeds being treated (2), remain in contact with any growing aquatic weeds being treated for at least several minutes, such as 5 minutes, and (3) remain in contact with any aquatic weed seed being treated through the germination period.

The aqueous herbicidal composition that is used for pre-emergent and/or post-emergent aquatic weed control may be prepared identically to the aqueous herbicidal composition that is used for terrestrial weed control. Therefore, the aqueous herbicidal composition may include water in addition to the purified form of glycine betaine that is available from Finn Sugar Bio-Products of Helsinki, Finland and/or the plant-derived product, such as CSB that is available from Midwest Agri-Commodities of Moorhead, Minn. Preferably, when the aqueous herbicidal composition is used for pre-emergent and/or post-emergent aquatic weed control, the herbicidal concentrate is the liquid version of NATURE'S WEED CONTROL™ herbicidal concentrate that is available from Greener Pastures Development Corporation of St. Paul, Minn. When used for pre-emergent and/or post-emergent control of aquatic weeds, the aqueous herbicidal composition may generally include about two parts by weight of the herbicidal concentrate for each part by weight of water.

The aqueous herbicidal composition may be applied at any rate, expressed in gallons of aqueous herbicidal composition per million gallons of water to be treated, that is effective for pre-emergent and post-emergent control of aquatic weeds. Though even a low application rate on the order of about ½ gallon, or even less, of the aqueous herbicidal composition per million gallons of water to be treated causes some degree of control of treated aquatic weeds and/or weed seeds, higher application rates tend to increase the eradication effect of the aqueous herbicidal composition on aquatic weeds and/or weed seeds and cause enhanced weed control.

For control of aquatic weeds, such as filamentous algae, the aqueous herbicidal composition is preferably applied to the aquatic weeds and/or seeds of the aquatic weeds at a rate ranging from about 2 gallons of the aqueous herbicidal composition per million gallons of water to be treated to about 7 gallons of aqueous herbicidal composition per million gallons of water to be treated, and is more preferably applied at a rate of about 5 gallons of the aqueous herbicidal composition per million gallons of water to be treated. Any conventional lawn or agricultural spraying equipment may be used to apply the aqueous herbicidal composition to the aquatic weeds and/or weed seeds.

Surprisingly, it has also been discovered that glycine betaine is effective for control of aquatic weeds that are responsible for diminished water clarity. When desiring to increase water clarity, glycine betaine, in the form of the herbicidal concentrate, such as the granular form of NATURE'S WEED CONTROL™ herbicidal concentrate, may be placed at the bottom of the aquatic environment, such as at the bottom of a lake or pond, in close proximity to the targeted weeds. The herbicidal concentrate may be placed in a dispensing container or package, such as a bio-degradable bag. Microorganisms, nutrient media, and/or ballast may optionally be included along with the herbicidal concentrate in the dispensing container. The dispensing container should permit mass transfer of the active ingredients (i.e. the naturally-occurring, plant-derived organic compound, such as glycine betaine) of the herbicidal concentrate and any included microorganisms and/or nutrient media out of the dispensing container and into the aquatic environment. The herbicidal concentrate is preferably in granular form to prevent seepage of the herbicidal concentrate from the dispensing container or package prior to placement in the aquatic environment.

The glycine betaine increases the metabolic rate of the microorganisms that are optionally included with the herbicidal concentrate in the dispensing container. Consequently, the microorganisms increase the rate of consumption of the same resources, such as phosphate soaps, carbon dioxide, water and light, that aquatic weeds typically consume. Increasing microorganism consumption of resources that are also required by the targeted aquatic weeds indirectly starves the aquatic weeds, and, thus, effectively controls the aquatic weeds that are present in the aquatic environment. Some non-exhaustive examples of microorganisms that may be included with the herbicidal concentrate to control aquatic weeds responsible for diminished water clarity in aquatic environments include *Bacillus subtillis* and Megaterium sp. One example of a commercially available microbial formulation that includes suitable microorganisms is the Formula Forty microbial blend that may be obtained from John Biesz Biological Products Company of Allentown, Pa.

Even if the microorganisms are not included in the dispensing container, the glycine betaine that is included as part of the herbicidal concentrate in the dispensing container has some killing effect on aquatic weeds that are responsible for diminished water clarity. However, significantly greater increases in water clarity are realized when the optional microorganisms are included along with glycine betaine in the dispensing container.

The optional nutrient media promotes logarithmic growth of the microorganisms and, thus, maximum consumption of resources by the microorganisms. Some examples of suitable components of the nutrient media include B-vitamins, such as thiamin (vitamin $B_1$), niacin, pyridoxine (vitamin $B_6$), riboflavin, and vitamin $B_{12}$; carbohydrates, such as dextrose, sucrose, galactose, glucose, fructose, lactose, and starch; lime; and potassium salts, such as potassium chloride, potassium iodide, and potassium polyacrylate. The components of the nutrient media may be individually supplied, or supplied in various prepared mixtures of two or more components that are subsequently combined to form the optional nutrient media. In one preferred form, the nutrient media includes, based on the total weight of the nutrient media, about 3 parts by weight dextrose, 1 part by weight potassium polyacrylate, one-half part by weight B-vitamins, and a pinch of lime, such as about one-tenth part of lime by weight.

The optional ballast may be any heavy material, such as rocks, planks, and/or sand, that helps stabilize and position the herbicidal concentrate, the optional microorganisms, and the optional nutrient media in the dispensing container at the bottom of the aquatic environment, such as the lake or pond. The dispensing container, such as the bio-degradable bag, that holds the aqueous herbicidal composition, optional microorganisms, optional nutrient media, and optional ballast may be made of any material that freely allows mass transfer of the glycine betaine, optional microorganisms, and optional nutrient media from the interior to the exterior of the dispensing container when placed in the aquatic environment, such as the bottom of lake or pond. Some examples of suitable materials that may be used to make the dispensing container include cotton; linen; nylon; and polyesters, such as DACRON® polyester and MYLAR® polyester; and any of these in any combination. Preferably, the dispensing container is the bio-degradable bag that is made of cotton.

The glycine betaine that is used to control aquatic weeds for the purpose of increasing water clarity may be supplied as part of the CLARIFY™ treatment system that is available from Greener Pastures Development Corporation of St. Paul, Minn. The CLARIFY™ system includes the microorganisms, the nutrient media, the ballast, the bio-degradable bag, and the granular form of NATURE'S WEED CONTROL™ herbicidal concentrate that supplies the glycine betaine. Each bag of the CLARIFY™ system typically weighs about two pounds and contains about ½ pound of the granular NATURE'S WEED CONTROL™ herbicidal concentrate; about 1 pound of the microorganisms; and about ½ pound of nutrient media and ballast.

One two pound bag of the CLARIFY™ treatment system may be used to treat from about 500 square feet of water surface to about 10,000 square feet of water surface when the average water depth beneath the water surface is about 3 to about 4 feet. When the average depth of the aquatic environment is greater than about 3 feet to about 4 feet, such as about 5 feet to about 10 feet, one or two additional two pound bags of the CLARIFY™ treatment system may be added to treat the water surface treatment range of about 500 square feet to about 10,000 square feet. The bags of the CLARIFY™ treatment system are preferably distributed uniformly at the bottom of the aquatic environment proximate the aquatic weeds responsible for the diminished water clarity.

The present invention is more particularly described in the following examples which are intended as illustrations only since numerous modifications and variations within the scope of the present invention will be apparent to those skilled in the art.

EXAMPLES

Example 1

This example illustrates a method of using glycine betaine as part of the aqueous herbicidal composition to control terrestrial weeds in accordance with the present invention. The aqueous herbicidal composition in this example included about one-half cup of NATURE'S WEED CONTROL™ herbicidal concentrate; about one quart of LIQUID COMPOST™ 1-1-3 fertilizer; about one pound of urea; and about 1.7 gallons of tap water. A plot of land containing an infestation of terrestrial weeds, such as creeping Charlie (*Glechoma hederaceae*), was treated using about 2.5 gallons of the aqueous herbicidal composition per thousand square feet. The treatment with the aqueous herbicidal composition killed the creeping Charlie and otherwise substantially ridded the terrestrial weeds from the treated plot of land.

The weed 10 that is depicted in FIG. 1 is an example of actively growing creeping Charlie prior to treatment with the aqueous herbicidal composition in accordance with this example. In the weed 10, the thylakoid membranes 14 and the outer membranes 16 of the chloroplasts 12 are intact, as would be expected of a healthy, actively growing weed. However, about 24 hours after treatment with the aqueous herbicidal composition in accordance with this example, the thylakoid membranes 14 (not shown in FIG. 2) and outer membranes 16 (not shown in FIG. 2) of the treated chloroplasts 12, as best depicted in FIG. 2, are ruptured and dissolved, rendering the thylakoid membranes 14 and the outer membranes 16 indiscernible and unidentifiable. The destruction of the thylakoid membranes 14 and outer membranes 16 of the treated chloroplasts 12 destroyed the ability of the creeping Charlie to produce energy required for metabolic processes, and thus killed the creeping Charlie. Bubbles 18 of oxygen trapped in the destroyed chloroplasts 12 are indicative of the increased rate of photosynthesis in the chloroplasts 12 that enhanced the herbicidal activity of the glycine betaine in the creeping Charlie.

Example 2

This example illustrates a method of using glycine betaine as part of the aqueous herbicidal composition to control terrestrial weeds in accordance with the present invention. The aqueous herbicidal composition in this example included about one-half cup of NATURE'S WEED CONTROL™ herbicidal concentrate; about one quart of LIQUID COMPOST™ 1-1-3 fertilizer; about one pound of urea; and about 1.7 gallons of tap water.

The aqueous herbicidal composition of this example was applied to a field 20 of turf grass 22 with many areas of dry exposed soil, extensive terrestrial weed 24 population, and some turf grass 22 (post-embryonic monocotyledonous plants) under severe moisture stress, as best depicted in FIG. 3. The aqueous herbicidal composition was applied to the field 20 at a rate of about 2½ gallons per thousand square feet. Rainfall occurred within about 5 minutes after application and the approximate amount of rainfall was 4 inches over a period of several hours.

Figure 4:
FIG. 4 is a photograph of the field depicted in FIG. 3 illustrating the effect of treating the weeds in accordance with the present invention using the aqueous herbicidal composition that contains glycine betaine.

The results after application of the aqueous herbicidal composition were spectacular in demonstrating the effectiveness of the aqueous herbicidal composition for control of terrestrial weeds. First, the turf grass 22 in the field 20 turned a vibrant green color within about 5 days after the initial and only application of the aqueous herbicidal composition, as best depicted in FIG. 4. Furthermore, the turf grass 22 grew and spread quickly, as evidenced by a massive reduction in bumpiness of the field 20 and a massive reduction of patches of bare ground. Also, the terrestrial weed 24 population was reduced to about 40% of the original terrestrial weed 24 population. Additionally, unwanted red clover and black medic terrestrial weeds were visually observed to be eliminated by the aqueous herbicidal composition application of this example.

Example 3

Figure 5:
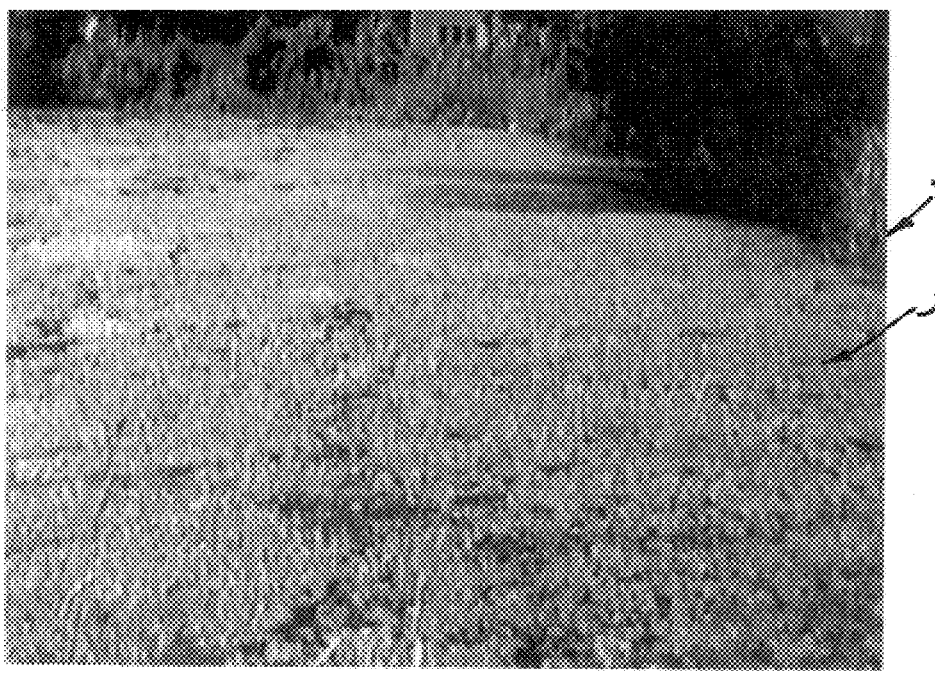
FIG. 5 is a photograph of weeds present in a pond before treatment with an herbicidal composition that contains glycine betaine.

This example illustrates a method of using glycine betaine as part of the aqueous herbicidal composition to control aquatic weeds in a pond 30, in which over 90% of the water surface was covered with filamentous algae 32, as best depicted in FIG. 5. The water in the pond 30 also had high levels of planktonic algae that greatly diminished water clarity in the pond 30. The glycine betaine was applied to the pond in two forms. The aqueous herbicidal composition was sprayed onto the surface of the pond, and bags of the CLARIFY™ treatment system were distributed about the bottom of the pond. The pond had a surface area of about six acres, an average depth of about 3 feet, and a volume of about six million gallons.

The aqueous herbicidal composition in this example included about two parts by weight of the liquid form of NATURE'S WEED CONTROL™ herbicidal concentrate and about one part by weight of tap water. About 30 gallons of the aqueous herbicidal composition was dispersed over the entire water surface of the pond 30. Additionally, 24 two pound bags of the CLARIFY™ treatment system were evenly distributed about the bottom of the pond. The bags of the CLARIFY™ treatment system included the microorganisms, the nutrient media, the ballast, the biodegradable bag, and the granular form of the NATURE'S WEED CONTROL™ herbicidal concentrate.

Figure 6:
FIG. 6 is a photograph of the pond depicted in FIG. 5 illustrating the effect of treating the weeds in accordance with the present invention with the herbicidal composition that contains glycine betaine.

Excellent control of aquatic weeds, as best depicted in FIG. 6, was observed within about seven days after application of the aqueous herbicidal composition of this example to the water surface of the pond 30. The filamentous algae 32 (not shown in FIG. 6) on the water surface of the pond was essentially eliminated in the pond 30. Furthermore, the amount of planktonic algae was also significantly reduced as demonstrated by a significant improvement of the water clarity in the pond 30 after treatment in accordance with this example.

Although the present invention has been described with reference to preferred embodiments, workers skilled in the art will recognize that changes may be made in form and detail without departing from the spirit and scope of the invention.

What is claimed is:

1. A method of controlling unwanted plants, the method comprising:

providing an herbicidal composition, the herbicidal composition comprising a naturally-occurring, plant-derived organic compound, the naturally-occurring, plant-derived organic compound being less toxic than common table salt;

applying the herbicidal composition to the unwanted plants; and applying a fertilizer to the unwanted plants prior to, during, or after application of the herbicidal composition to the unwanted plants, the fertilizer causing increased uptake of the naturally-occurring, plant-derived organic compound by the unwanted plants.

2. The method of claim 1 wherein the naturally-occurring, plant-derived organic compound has an $LD_{50}$ that is greater than about 11,000 mg of the naturally-occurring, plant-derived organic compound per kilogram of rat body weight when the naturally-occurring, plant-derived organic compound is orally administered to rats.

3. The method of claim 1 wherein the unwanted plants cause diminished water clarity in a body of water, the naturally-occurring, plant-derived organic compound increasing the water clarity after application of the herbicidal composition to the unwanted plants.

4. The method of claim 1 wherein the herbicidal composition comprises a molasses processing byproduct that is derived from sugar beets.

5. A method of controlling aquatic weeds, the method comprising:

providing an herbicidal composition, the herbicidal composition comprising a naturally-occurring, plant-derived organic compound; and applying the herbicidal composition to the aquatic weeds, the naturally-occurring, plant-derived organic compound capable of increasing water clarity without harming fish or amphibians present in the water.

6. The method of claim 5 wherein the naturally-occurring, plant-derived organic compound is less toxic than common table salt.

7. The method of claim 5, the method further comprising applying a fertilizer to the aquatic weeds prior to, during, or after application of the herbicidal composition to the aquatic weeds, the fertilizer causing increased uptake of the naturally-occurring, plant-derived organic compound by the aquatic weeds.

8. The method of claim 5 wherein the herbicidal composition comprises a molasses processing byproduct that is derived from sugar beets.

9. A method of improving water clarity in a body of water, the method comprising:

providing an herbicidal composition, the herbicidal composition comprising a naturally-occurring, plant-derived organic compound; and distributing the herbicidal composition in the body of water where water clarity is diminished, the naturally-occurring, plant-derived organic compound effective to enhance the diminished water clarity.

10. The method of claim 9 wherein the naturally-occurring, plant-derived organic compound is glycine betaine.

11. The method of claim 9 wherein the naturally-occurring, plant-derived organic compound is capable of increasing the water clarity without harming fish or amphibians present in the body of water.

12. The method of claim 9 wherein the naturally-occurring, plant-derived organic compound has an $LD_{50}$ that is greater than about 11,000 mg of the naturally-occurring, plant-derived organic compound per kilogram of rat body weight when the naturally-occurring, plant-derived organic compound is orally administered to rats.

13. A method of controlling unwanted plants, the method comprising:

providing an herbicidal composition, the herbicidal composition comprising a naturally-occurring, plant-derived organic compound, the naturally-occurring, plant-derived organic compound being less toxic than common table salt; and applying the herbicidal composition to the unwanted plants, the unwanted plants causing diminished water clarity in a body of water, the naturally-occurring, plant-derived organic compound increasing the water clarity after application of the herbicidal composition to the unwanted plants.

14. The method of claim 13 wherein the naturally-occurring, plant-derived organic compound has an $LD_{50}$ that is greater than about 11,000 mg of the naturally-occurring, plant-derived organic compound per kilogram of rat body weight when the naturally-occurring, plant-derived organic compound is orally administered to rats.

15. The method of claim 13 wherein the naturally-occurring, plant-derived organic compound kills the unwanted plants after the herbicidal composition is applied to the unwanted plants.

16. A method of controlling unwanted plants, the method comprising:

providing an herbicidal composition, the herbicidal composition comprising a naturally-occurring, plant-derived organic compound; and applying the herbicidal composition to the unwanted plants, the naturally-occurring, plant-derived organic compound killing the unwanted plants after the herbicidal composition is applied to the unwanted plants; and applying a fertilizer to the unwanted plants prior to, during, or after application of the herbicidal composition to the unwanted plants, the fertilizer causing increased uptake of the naturally-occurring, plant-derived organic compound by the unwanted plants.

17. The method of claim 16 wherein the naturally-occurring, plant-derived organic compound is less toxic than common table salt.

18. The method of claim 16 wherein the herbicidal composition comprises a molasses processing byproduct that is derived from sugar beets.

19. A method of controlling aquatic weeds, the method comprising:

providing an herbicidal composition, the herbicidal composition comprising a naturally-occurring, plant-derived organic compound;

applying the herbicidal composition to the aquatic weeds;

applying a fertilizer to the aquatic weeds prior to, during, or after application of the herbicidal composition to the aquatic weeds, the fertilizer causing increased uptake of the naturally-occurring, plant-derived organic compound by the aquatic weeds.

20. The method of claim 19 wherein the naturally-occurring, plant-derived organic compound is less toxic than common table salt.

21. A method of controlling dicotyledonous plants, the method comprising:

providing an herbicidal composition, the herbicidal composition comprising a naturally-occurring, plant-derived organic compound;

applying the herbicidal composition to the dicotyledonous plants, the herbicidal composition effective for killing any dicotyledonous plant and post-embryonic monocotyledonous plants not harmed by the herbicidal composition; and applying a fertilizer to the dicotyledonous plants prior to, during, or after application of the herbicidal composition to the dicotyledonous plants, the fertilizer causing increased uptake of the naturally-occurring, plant-derived organic compound by the dicotyledonous plant.

22. The method of claim 21 wherein the naturally-occurring, plant-derived organic compound is glycine betaine.

23. The method of claim 21 wherein the naturally-occurring, plant-derived organic compound is less toxic than common table salt.

24. A method of controlling unwanted plants, the method comprising:

providing an herbicidal composition, the herbicidal composition comprising a molasses processing byproduct that is derived from sugar beets, the molasses processing byproduct comprising a naturally-occurring, plant-derived organic compound, the naturally-occurring, plant-derived organic compound being less toxic than common table salt; and applying the herbicidal composition to the unwanted plants.

25. The method of claim 24 wherein the naturally-occurring, plant-derived organic compound kills the unwanted plants after the herbicidal composition is applied to the unwanted plants.

26. A method of controlling unwanted plants, the method comprising:

providing an herbicidal composition, the herbicidal composition comprising a molasses processing byproduct that is derived from sugar beets, the molasses processing byproduct comprising a naturally-occurring, plant-derived organic compound; and applying the herbicidal composition to the unwanted plants, the naturally-occurring, plant-derived organic compound killing the unwanted plants after the herbicidal composition is applied to the unwanted plants.

27. A method of controlling aquatic weeds, the method comprising:

providing an herbicidal composition, the herbicidal composition comprising, a molasses processing byproduct that is derived from sugar beets, the molasses processing byproduct comprising a naturally-occurring, plant-derived organic compound; and applying the herbicidal composition to the aquatic weeds.

28. The method of claim 27 wherein the naturally-occurring, plant-derived organic compound is less toxic than common table salt.

29. A method of controlling unwanted plants, the method comprising:

providing an herbicidal composition, the herbicidal composition comprising a naturally-occurring, plant-derived organic compound, the naturally-occurring, plant-derived organic compound being a quarternary ammonium salt, the herbicidal composition comprising a molasses processing byproduct that is derived from sugar beets; and applying the herbicidal composition to the unwanted plants.

30. A method of controlling unwanted plants, the method comprising:

providing an herbicidal composition, the herbicidal composition comprising a naturally-occurring, plant-derived organic compound, the naturally-occurring, plant-derived organic compound being a quarternary ammonium salt;

applying the herbicidal composition to the unwanted plants; and applying a fertilizer to the unwanted plants prior to, during, or after application of the herbicidal composition to the unwanted plants, the fertilizer causing increased uptake of the naturally-occurring, plant-derived organic compound by the unwanted plants.

31. A method of controlling unwanted plants, the method comprising:

providing an herbicidal composition, the herbicidal composition comprising a naturally-occurring, plant-derived organic compound, the naturally-occurring, plant-derived organic compound being a quarternary ammonium salt; and applying the herbicidal composition to the unwanted plants, the unwanted plants causing diminished water clarity in a body of water, the naturally-occurring, plant-derived organic compound increasing the water clarity after application of the herbicidal composition to the unwanted plants.

32. A method of controlling unwanted plants, the method comprising:

providing an herbicidal composition, the herbicidal composition comprising a naturally-occurring, plant-derived organic compound, the naturally-occurring, plant-derived organic compound being a quarternary ammonium salt; and applying the herbicidal composition to the unwanted plants, wherein the naturally-occurring, plant-derived organic compound kills the unwanted plants after the herbicidal composition is applied to the unwanted plants.

33. A method of controlling unwanted plants, the method comprising:

providing an herbicidal composition, the herbicidal composition comprising a naturally-occurring, plant-derived organic compound, the naturally-occurring, plant-derived organic compound comprising glycine betaine; and applying the herbicidal composition to the unwanted plants.

34. The method of claim 33, the method further comprising applying a fertilizer to the unwanted plants prior to, during, or after application of the herbicidal composition to the unwanted plants, the fertilizer causing increased uptake of the naturally-occurring, plant-derived organic compound by the unwanted plants.

35. The method of claim 33 wherein the unwanted plants cause diminished water clarity in a body of water, the naturally-occurring, plant-derived organic compound increasing the water clarity after application of the herbicidal composition to the unwanted plants.

36. The method of claim 33 wherein the naturally-occurring, plant-derived organic compound kills the unwanted plants after the herbicidal composition is applied to the unwanted plants.

37. A method of controlling unwanted plants, the method comprising:

providing an herbicidal composition, the herbicidal composition comprising a naturally-occurring, plant-derived organic compound, the naturally-occurring, plant-derived organic compound being glycine betaine; and applying the herbicidal composition to the unwanted plants, the naturally-occurring, plant-derived organic compound killing the unwanted plants after the herbicidal composition is applied to the unwanted plants.

38. The method of claim 37 wherein the naturally-occurring, plant-derived organic compound is less toxic than common table salt.

39. The method of claim 37, the method further comprising applying a fertilizer to the unwanted plants prior to, during, or after application of the herbicidal composition to the unwanted plants, the fertilizer causing increased uptake of the naturally-occurring, plant-derived organic compound by the unwanted plants.

40. The method of claim 37 wherein the herbicidal composition comprises a molasses processing byproduct that is derived from sugar beets.

41. A method of controlling dicotyledonous plants, the method comprising:

providing an herbicidal composition, the herbicidal composition comprising a naturally-occurring, plant-derived organic compound, the naturally-occurring, plant-derived organic compound being glycine betaine; and applying the herbicidal composition to the dicotyledonous plants, the herbicidal composition effective for killing any dicotyledonous plant and post-embryonic monocotyledonous plants not harmed by the herbicidal composition.

42. The method of claim 41, the method further comprising applying a fertilizer to the dicotyledonous plants prior to, during, or after application of the herbicidal composition to the dicotyledonous plants, the fertilizer causing increased uptake of the naturally-occurring, plant-derived organic compound by the dicotyledonous plant.

43. The method of claim 41 wherein the naturally-occurring, plant-derived organic compound is less toxic than common table salt.

44. A method of killing weeds, the method comprising:

providing an herbicidal composition, the herbicidal composition comprising glycine betaine; and applying the herbicidal composition to the weeds, the glycine betaine effective to kill the weeds.

45. The method of claim 44 wherein:

the herbicidal composition is effective for killing any dicotyledonous plant; and post-embryonic monocotyledonous plants are not harmed by the herbicidal composition.

* * * * *